United States Patent [19]

Zakharova et al.

[11] 4,122,287
[45] Oct. 24, 1978

[54] METHOD OF PREPARING 2,6-DI-TERT.BUTYL-4-METHYLPHENOL

[76] Inventors: Nina Vasilievna Zakharova; Alexandr Grigorievich Liakumovich, both of ulitsa Galeeva, 10, kv. 8, Kazan; Jury Ivanovich Michurov, prospekt Lenina, 13, kv. 4; Zoya Stepanovna Shalimova, ulitsa Druzhby, 19, kv. 56, both of Sterlitamak, all of U.S.S.R.

[21] Appl. No.: 769,116
[22] Filed: Feb. 16, 1977
[51] Int. Cl.$^2$ .............................................. C07C 39/06
[52] U.S. Cl. ................................................... 568/784
[58] Field of Search ........... 260/624 R, 621 R, 624 C, 260/619 R

[56] References Cited

U.S. PATENT DOCUMENTS

| 2,841,624 | 7/1958 | Norton et al. ............... 260/624 R |
| 2,882,319 | 4/1959 | Hotelling et al. ............. 260/624 R |
| 3,845,143 | 10/1974 | Wollensak ................... 260/624 C |

Primary Examiner—James O. Thomas, Jr.
Attorney, Agent, or Firm—Lackenbach, Lilling & Siegel

[57] ABSTRACT

A method of preparing 2,6-di-tert.butyl-4-methylphenol comprising reacting 2,6-di-tert.butylphenol with formaldehyde and dimethylamine in a medium of methanol or ethanol at a temperature within the range of from 80° to 90° C to give a reaction mass containing N,N-dimethyl-3,5-di-tert.butyl-4-hydroxybenzylamine and readily-volatile products such as methanol or ethanol, water and bis-amine. The readily-volatile products are removed from the reaction mass by heating thereof to a temperature within the range of from 110° to 140° C simultaneously with purging the reaction mass with an inert gas containing a secondary amine in an amount of from 5 to 50% by volume. Thereafter, N,N-dimethyl-3,5-di-tert.butyl-4-hydroxybenzylamine is contacted with hydrogen at a molar ratio therebetween of 1:4–10 respectively on a hydrogenation catalyst at a temperature ranging from 120° to 160° C, to give the desired product which is then isolated.

The method according to the present invention makes it possible to increase the desired product yield and improve quality thereof as compared to the prior art methods. The yield of the desired product is 98.7% as calculated per the starting raw materials. The method is technologically simple.

4 Claims, No Drawings

METHOD OF PREPARING 2,6-DI-TERT.BUTYL-4-METHYLPHENOL

The present invention relates to methods of preparing 2,6-di-tert.butyl-4-methylphenol.

The latter is widely employed as an antioxidant in petroleum products, oils, rubbers, plastics and other polymeric materials. It is also useful in food-stuff industry for stabilization of animals fats, polymeric materials of medicinal application adapted to be in contact with food products (polyethylene film, rubber for soothers and the like); it finds also a wide application in medicine as a remedy for treating certain cancerous diseases. Furthermore, it is useful for stabilization of animal feeds.

Known in the art are several methods for preparing 2,6-di-tert.butyl-4-methylphenol. Thus, there is a method based on the use of p-cresol as the starting product. The latter is alkylated with olefins on various catalysts, mainly sulfuric acid.

However, p-cresol is scarcely available and rather expensive product; furthermore, it always contains other isomers, wherefore alkylation thereof results in a mixture of alkylphenols which is difficult to separate.

The process is performed in several stages; it also requires the use of concentrated sulphuric acid. The method also results in a large amount of by-products and waste waters.

Also known in the art is a method of preparing 2,6-di-tert.butyl-4-methylphenol by condensation of 2,6-di-tert.butylphenol with formaldehyde and dimethylamine with the formation of N,N-dimethyl-3,5-di-tert.butyl-4-hydroxybenzylamine (Mannich base) and hydrogenolysis thereof.

The method contemplates condensation of 2,6-di-tert.butylphenol with formaldehyde and dimethylamine in an aquo-alcoholic solution in the molar ratio of the starting components of 1:1:1 at a temperature of 80° to 90° C.

As a result, the following reaction occurs:

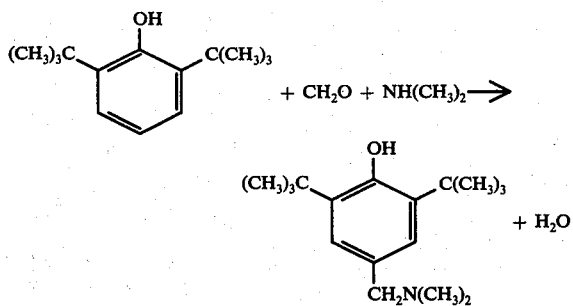

During the process, the resulting reaction mass containing a Mannich base, methanol, water and amines is heated to a temperature within the range of from 110° to 140° C. to distill off the major portion of readily-volatile products, i.e. methanol, water and amines. The Mannich base is contacted with hydrogen at a temperature of up to 200° C. on any suitable hydrogenation catalyst (e.g. those containing palladium, platinum, nickel). Therewith, hydrogenation of the Mannich base occurs according to the following scheme:

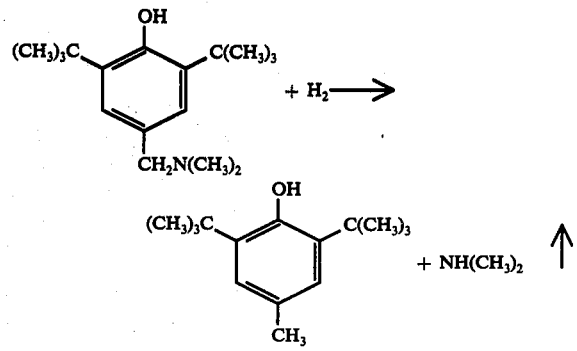

This prior art process features, as its principal advantages, the use of cheap and readily-available raw materials (2,6-di-tert.butylphenol, formaldehyde, dimethylamine), absence of corroding media, small amounts of waste waters.

A disadvantage of this prior art process resides in the formation of heavy condensation products of the Mannich base at the stage of the removal of readily-volatile products.

The Mannich base, representing a thermally non-stable compound, is partly decomposed, upon heating thereof to a temperature above 100° C., with the formation of methylenequinone and dimethylamine. The decomposition reaction is accelerated with increasing temperature. The reaction is irreversible and proceeds according to the following scheme:

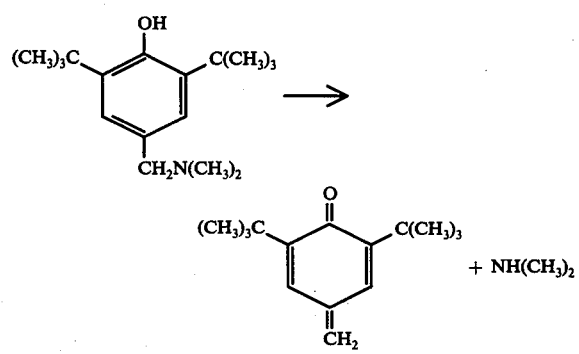

Dimethylamine is removed from the reaction mass along with the readily-volatile products.

Methylenequinone comprises a highly reactive product which becomes instantly involved in various disproportionation reactions:

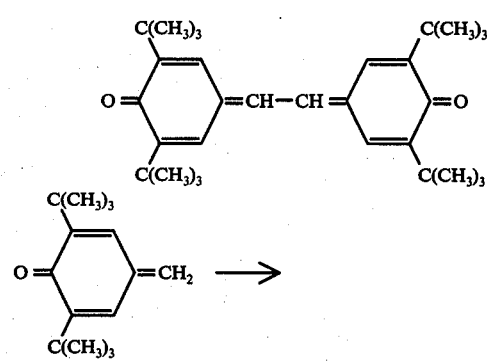

-continued

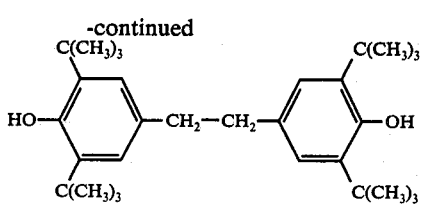

The reaction products substantially comprise dimethylamine and high-boiling disproportionation products of methylenequinone. As a consequence, the yield and purity of the desired product are impaired. Isolation of the desired product is effected by conventional methods (such as distillation, recrystallization).

Furthermore, amines exert a poisonous effect on the hydrogenation catalyst thus reducing its life time. in the presence of amines the catalyst operates at temperatures exceeding 160° C.

It is an object of the present invention to provide such a method of preparing 2,6-di-tert.butyl-4-methylphenol which would enable the production, by a rather simple technology, of the desired product possessing a higher quality and with a greater yield.

These and other objects of the present invention are accomplished by a method, wherein 2,6-di-tert.butylphenol is reacted with formaldehyde and dimethylamine in a medium of methanol or ethanol at a temperature of from 80° to 90° C. with the formation of a reaction mass containing N,N-dimethyl-3,5-di-tert.butyl-4-hydroxybenzylamine and readily-volatile products, i.e. methanol or ethanol, water and bis-amine, followed by the removal of the readily-volatile products from this reaction mass by heating thereof to a temperature of 110° to 140° C. and contacting N,N-dimethyl-3,5-di-tert.butyl-4-hydroxybenzylamine with hydrogen at a molar ratio therebetween of 1:4–10 respectively on a hydrogenation catalyst at a temperature ranging from 120° to 160° C. with the formation of the desired product and subsequent isolation thereof; according to the present invention, heating of the reaction mass is effected simultaneously with purging thereof with an inert gas containing a secondary amine in an amount ranging from 5 to 50% by volume.

Upon intermixing of 2,6-di-tert.butyl-4-methylphenol, formaldehyde and dimethylamine in an alcoholic medium at a temperature within the range of from 80° to 90° C. a condensation reaction occurs resulting in the formation of N,N-dimethyl-3,5-di-tert.butyl-4-hydroxybenzylamine. Along with the latter, formed are readily-volatile reaction products, i.e., water and bis-amine. In addition, alcohol is contained in the reaction mass. The thus-selected temperature range is optimal. When temperature is decreased below the lower limit, the reaction rate of condensation is substantially reduced. Upon increasing temperature above 90° C., decomposition of the Mannich base is observed.

The alcohols selected according to the present invention ensure a homogeneous character of the reaction mass. When higher-boiling alcohols are employed, the reaction mass becomes stratified.

To ensure favorable conditions for hydrogenation of the Mannich base, water and bis-amine should be removed from the hydrogenation zone, since they poison the catalyst, and the bis-amine is subjected to hydrogenation. Furthermore, in the presence of water the Mannich base is especially readily decomposed with the formation of heavy reaction products.

As it has been mentioned hereinabove, the readily-volatile products are removed from the reaction mass at a temperature within the range of from 110° to 140° C. with simultaneously purging with an inert gas containing a secondary amine in an amount of from 5 to 50% by volume. At a temperature below 110° C. the time for the removal of said readily-volatile products is substantially increased. Increasing temperature above 140° C. at this process stage results in decomposition of the Mannich base. Content of the secondary amine in the inert gas prevents the product from decomposition under the above-mentioned conditions; however, it should not be below 0.5% by volume, since in this case the decomposition process is not completely inhibited, and not above 50% by volume, since otherwise the readily-volatile products could not be completely distilled-off.

As the hydrogenation catalyst use may be made of any conventional hydrogenation catalysts such as palladium-on-carbon, palladium-on-alumina, platinum-on-alumina, nickel-copper supported by alumina, skeleton-like (alloyed) nickel catalysts, nickel-on-kieselguhr. In respect of their service life and stability in operation, it is preferable to employ skeleton nickel catalysts.

Said conditions for hydrogenation of Mannich base, i.e., temperature of from 120° to 160° C. and molar ratio of N,N-dimethyl-3,5-di-tert.butyl-4-hydroxybenzylamine of 1:4–10, are optimal. Under these conditions the Mannich base is hydrogenated to 2,6-di-tert.butyl-4-methylphenol. At a temperature below 120° C. the hydrogenation reaction does not proceed to the end, whereby the desired product yield is reduced. Increasing temperature above the upper limit also exerts a detrimental effect on the desired product yield, since under these conditions its partial hydrogenation occurs. The selected molar ratio of the Mannich base to hydrogen also provides for a required rate of the hydrogenation reaction with the optimal volume of the reaction zone.

It is advisable to employ, as the inert gas, hydrogen, nitrogen, helium, argon, $C_1$–$C_5$ hydrocarbons. All these gases give the same effect, though hydrogen is preferred for the technological considerations.

As the secondary amine it is advisable to employ dimethylamine, diethylamine.

The secondary amine content in the inert gas should preferably vary from 15 to 30% by volume.

The method of preparing 2,6-di-tert.butyl-4-methylphenol according to the present invention, as compared to the prior art methods, makes it possible to prevent the Mannich base from thermal decomposition thus resulting in an increased yield of the desired product and improved quality thereof.

Thus, the desired product yield in the prior art method is 94.0%. Besides, it contains microimpurities of quinones which impart yellow color to the product and substantially hinder purification thereof.

The desired product yield in the method according to the present invention is 98.7%; after separation, a white-color product is obtained.

The process is technologically simple and performed preferably in the following manner.

Formaldehyde and dimethylamine are mixed in an equimolar ratio. The resulting mixture is cooled to a temperature of from 5° to 8° C. This mixture is added to the equimolar amount of 2,6-di-tert.butylphenol in the form of its alcoholic solution (alcohol is employed for making the mixture homogeneous). The mixture of the starting monomers is heated to a temperature within the range of from 80° to 90° C., preferably from 80° to 85° C., and maintained at this temperature for a period of 3 to 6 hours. As a result, a reaction mass is obtained containing the Mannich base, water and bis-amine. The reaction mass is heated to a temperature within the range of from 110° to 140° C., and purged with an inert gas containing a secondary amine to remove readily-volatile products. The Mannich base exempted from the readily-volatile products is contacted with hydrogen on any conventional hydrogenation catalyst to obtain a catalysate containing 2,6-di-tert.butyl-4-methylphenol. Recovery of the desired product is performed by conventional methods. To this end, the catalysate is separated from the catalyst and subjected to distillation under a pressure of from 15 to 30 mm Hg at a temperature within the range of from 140° to 180° C. Remaining in the still are heavy reaction products and unreacted Mannich base. The distillate comprises the reaction product. For the purpose of an additional purification the desired product is subjected to recrystallization.

For a better understanding of the present invention some specific Examples are given hereinbelow.

EXAMPLE 1

Into a round-bottom flask provided with a thermometer, reflux condenser, stirrer and an inlet pipe for the supply of 2,6-di-tert.butylphenol there are charged, under stirring, 30 g of formaldehyde and 45 g of dimethylamine. The mixture is cooled to 5°–8° C., maintained at this temperature for 1 hour and then 206 g of 2,6-di-tert.butylphenol in the form of a 70% ethanolic solution are added thereto. The resulting mixture is heated to a temperature of 85° C. and maintained at this temperature for 3 hours. Thereafter the reaction mass is transferred to a reactor provided with a Schott filter in its lower section for a better distribution of gas. The reactor is also provided with a thermometer and a trap. The reactor is placed into a thermostat with a temperature of 120° C., and the reaction mass is purged with hydrogen containing 20% by volume of dimethylamine for 0.5 hour. Under these conditions, distilling of the readily-volatile products is observed which are then entrapped by the trap cooled by carbon dioxide.

On completion of the distillation, the mixture from the flask is transferred to an autoclave provided with a stirrer and an inlet pipe for the supply of hydrogen and an outlet pipe for the removal of hydrogen in excess along with gaseous reaction products.

Charged into the autoclave is Raney nickel at a molar ratio of the Mannich base to hydrogen of 1:7. The reactor contents are heated to a temperature of 120° C. Under these conditions the Mannich base is hydrogenated with hydrogen in excess and gaseous reaction products are evacuated from the reactor.

To recover the desired product, the catalysate is separated from the catalyst by filtration and distilled at a still temperature of 160° C. under a pressure of 20 mm Hg. Remained in the still are 2.9 g of heavy reaction products and non-reacted Mannich base; the distillate contained 217.1 g of the desired product which corresponds to 98.7% by weight of the theoretical value.

For an additional purification the desired product is subjected to recrystallization to give 208.3 g of pure desired product which corresponds to 94.7% of the theoretical value.

For the comparison purposes, under the same conditions there was obtained 2,6-di-tert.butyl-4-methylphenol, without, however, purging volatile products out of the reaction mass after condensation of 2,6-di-tert.butyl-4-methylphenol with formaldehyde and dimethylamine. After distillation there were recovered 204.8 g of the desired product (94% of the theoretical value).

EXAMPLES 2 to 23

Preparation of 2,6-di-tert.butyl-4-4-methylphenol is effected like in Example 1. The process conditions are shown in the following Table.

| | Condensation conditions | | Conditions for the removal of readily-volatile products | | | Secondary amine content in inert gas, vol.% | Hydrogenation conditions | | | |
|---|---|---|---|---|---|---|---|---|---|---|
| No. 1 | Temperature, °C 2 | Alcohol 3 | Temperature, °C 4 | Inert gas 5 | Secondary amine 6 | 7 | Temperature, °C 8 | Catalyst 9 | Molar ratio between Mannich base and hydrogen 10 | The desired product yield, vol% 11 |
| 2 | 80 | ethanol | 120 | hydrogen | dimethylamine | 20 | 120 | Raney nickel | 1:7 | 98.6 |
| 3 | 90 | ethanol | 120 | hydrogen | dimethylamine | 20 | 120 | Raney nickel | 1:7 | 98.4 |
| 4 | 85 | methanol | 120 | hydrogen | dimethylamine | 20 | 120 | Raney nickel | 1:7 | 98.7 |
| 5 | 85 | methanol | 140 | hydrogen | dimethylamine | 20 | 120 | Raney nickel | 1:7 | 98.1 |
| 6 | 85 | methanol | 110 | hydrogen | dimethylamine | 20 | 120 | Raney nickel | 1:7 | 98.6 |
| 7 | 85 | methanol | 120 | hydrogen | dimethylamine | 20 | 160 | Raney nickel | 1:7 | 98.6 |
| 8 | 85 | methanol | 120 | hydrogen | dimethylamine | 5 | 120 | Raney nickel | 1:7 | 98.4 |
| 9 | 85 | methanol | 120 | hydrogen | dimethylamine | 50 | 120 | Raney nickel | 1:7 | 98.6 |
| 10 | 85 | methanol | 120 | argon | dimethylamine | 20 | 120 | Raney nickel | 1:7 | 98.7 |
| 11 | 85 | methanol | 120 | nitrogen | dimethylamine | 20 | 120 | Raney nickel | 1:7 | 98.7 |
| 12 | 85 | methanol | 120 | methane | dimethylamine | 20 | 120 | Raney nickel | 1:7 | 98.7 |
| 13 | 85 | methanol | 120 | hydrogen | diethylamine | 20 | 120 | Raney nickel | 1:7 | 98.7 |
| 14 | 85 | methanol | 120 | hydrogen | dimethylamine | 20 | 120 | palladium-on-carbon | 1:7 | 98.6 |
| 15 | 85 | methanol | 120 | hydrogen | dimethylamine | 20 | 120 | palladium-on-alumina | 1:7 | 98.7 |
| 16 | 85 | methanol | 120 | hydrogen | dimethylamine | 20 | 120 | platinum- | 1:7 | 98.8 |

-continued

| | Condensation conditions | | Conditions for the removal of readily-volatile products | | | Secondary amine content in inert gas, vol.% | Hydrogenation conditions | | | |
|---|---|---|---|---|---|---|---|---|---|---|
| No. 1 | Temperature, °C 2 | Alcohol 3 | Temperature, °C 4 | Inert gas 5 | Secondary amine 6 | 7 | Temperature, °C 8 | Catalyst 9 | Molar ratio between Mannich base and hydrogen 10 | The desired product yield, vol% 11 |
| 17 | 85 | methanol | 120 | hydrogen | dimethylamine | 20 | 120 | nickel-copper on-alumina | 1:7 | 98.8 |
| 18 | 85 | methanol | 120 | hydrogen | dimethylamine | 20 | 120 | Raney nickel on alumina | 1:4 | 98.6 |
| 19 | 85 | methanol | 120 | hydrogen | dimethylamine | 20 | 120 | Raney nickel | 1:10 | 98.7 |
| 20 | 85 | methanol | 120 | hydrogen | dimethylamine | 20 | 140 | Raney nickel | 1:7 | 98.8 |
| 21 | 85 | methanol | 120 | hydrogen | dimethylamine | 10 | 120 | Raney nickel | 1:7 | 98.6 |
| 22 | 85 | methanol | 120 | helium | dimethylamine | 20 | 120 | Raney nickel | 1:7 | 98.6 |
| 23 | 85 | methanol | 120 | ethane | dimethylamine | 20 | 120 | Raney nickel | 1:7 | 98.6 |

What is claimed is:

1. A method of preparing 2,6-di-tert.butyl-4-methylphenol which comprises reacting 2,6-di-tert.butylphenol with formaldehyde and dimethylamine in a medium of an alcohol selected from the group consisting of methanol and ethanol at a temperature ranging from 80° to 90° C. with the formation of a reaction mass containing N,N-dimethyl-3,5-di-tert.butyl-4-hydroxybenzylamine and readily-volatile products, viz. an alcohol selected from the group containing methanol and ethanol, water and bis-amine; removing said readily-volatile products from the resulting reaction mass by heating thereof to a temperature ranging from 110° to 140° C. simultaneously with purging said reaction mass with an inert gas containing a secondary amine in an amount ranging from 5 to 50% by volume; contacting the remaining N,N-dimethyl-3,5-di-tert.butyl-4-hydroxybenzylamine with hydrogen at a molar ratio therebetween of 1:4-10 respectively on a hydrogenation catalyst at a temperature ranging from 120° to 160° C. with the formation of the desired product; and isolation of the latter.

2. A method as claimed in claim 1, wherein as the inert gas use is made of a gas selected from the group consisting of hydrogen, nitrogen, helium, argon and $C_1$-$C_5$ hydrocarbons.

3. A method as claimed in claim 1, wherein as the secondary amine use is made of an amine selected from the group consisting of dimethylamine and diethylamine.

4. A method as claimed in claim 1, wherein said inert gas contains 15 to 30% by volume of said secondary amine.

* * * * *